United States Patent [19]

Saitou et al.

[11] Patent Number: 5,080,911
[45] Date of Patent: Jan. 14, 1992

[54] PROCESS FOR MODIFYING THE PROPERTIES OF EGG YOLK

[75] Inventors: Chiaki Saitou, Tokyo; Kozo Ouchi, Saitama; Shigenori Ohta, Tokyo, all of Japan

[73] Assignee: Kyowa Hakko Kogyo Kabushiki Kaisha, Japan

[21] Appl. No.: 525,496

[22] Filed: May 17, 1990

[30] Foreign Application Priority Data

May 17, 1989 [JP] Japan .................. 1-123462

[51] Int. Cl.$^5$ .................. A23J 1/08; A23J 7/00
[52] U.S. Cl. .................. 426/32; 426/47; 426/602; 426/605; 426/613; 426/654
[58] Field of Search .......... 426/32, 47, 602, 605, 426/613, 654

[56] References Cited

U.S. PATENT DOCUMENTS 3,260,606  7/1966  Azuma .................. 426/47
4,034,124  7/1977  van Dam .................. 426/602
4,478,866  10/1984  Ohta et al. .................. 426/26

FOREIGN PATENT DOCUMENTS 3493772  9/1972  Japan .

OTHER PUBLICATIONS

Dutilh et al., "Improvement of Product Attributes of Mayonnaise by Enzymatic Hydrolysis of Egg Yolk with Phospholipase $A_2$", J. Science of Food and Agriculture, 32, 451–458, 1981, Primary Examiner—Marianne Cintins
Attorney, Agent, or Firm—Schweitzer, Cornman & Gross

[57] ABSTRACT

A process for modifying the properties of egg yolk, which comprises treating egg yolk with an effective amount of phospholipase D derived from a microorganism, thereby to convert phospholipids contained in said egg yolk into phosphatidic acid.

14 Claims, No Drawings

PROCESS FOR MODIFYING THE PROPERTIES OF EGG YOLK

FIELD OF THE INVENTION

The present invention relates to processes for modifying the properties of egg yolk for use in foodstuffs.

BACKGROUND OF THE INVENTION

Egg yolk is used in the preparation of foodstuffs by virtue of its excellent properties such as emulsification and heat-gelation It was known that the functional properties of egg yolk for use in the preparation of foodstuffs depend particularly upon lipoprotein which is a higher structure containing about 15% w/w of proteins and 10% w/w of phospholipids. Phosphatidyl choline (PC) and phosphatidyl ethanolamine (PE) are known to be prevalent in the phospholipids of egg yolk; the following Table 1 indicates typical phospholipids present in hen egg yolk:

TABLE 1

| Phosphatidyl choline (PC) | 84.3 (mol %) |
|---|---|
| Phosphatidyl ethanolamine (PE) | 11.9 |
| Sphingomyelin | 1.9 |
| Lysophosphatidyl choline | 1.9 |

(Source: Food Chemical, Vol. 1, No. 7, page 76, 1985)

It is also known to modify the properties of egg yolk by treatment with a phospholipase. For example, JP-A-84785/76 corresponding to U.S. Pat. No. 4,034,124 discloses an emulsion containing a phospholipoprotein which has been modified by the action phospholipase A (PL-A), which is prepared by a process comprising subjecting a phospholipoprotein to the action of PL-A at a temperature of 60°-90° C. to give a specified ratio of conversion. In this case, the material containing phospholipoprotein is preferably whole egg or egg yolk. The resultant emulsions exhibit increased heat-stability.

This patent also describes the use of phospholipase D (PL-D), commercially available from Sigma, U.S.A. It appears that the particular mentioned PL-D does not originate from a microorganism but is of plant origin, since no PL-D originating from microorganism (for instance, a microorganism of the genus Streptomyces) was ever mentioned in the Sigma catalogues published earlier than 1986.

Japanese Patent Publication 34937/72 discloses that the heat-coagulation of egg albumen and yolk, contained in foodstuffs which are prepared by processing hens eggs, can be prevented by treating a solution of whole egg or egg yolk with an enzyme at a pH of 3.5-4.5 until the heat-coagulating properties disappear. The enzymes which may be used are obtained from molds such as Aspergillus and Rhizopus. However the enzyme-treated egg is obviously not preferred for use in the preparation of certain foodstuffs which require the heat-gelation properties.

In JP-A-51853/83 corresponding to U.S. Pat. No. 4,478,866, lysophosphatidic acid (LPA) was disclosed as being particularly advantageous as an emulsifier for use in farinaceous foodstuffs such as doughs and that such an emulsifier may be partly comprised of lysophosphatidic acid (LPA) which may be prepared by treating phospholipids with PL-D and PL-A. This patent discloses the use of PL-D derived from plants but not the use of PL-D derived from microorganisms.

Journal of the Science of Food and Agriculture, 32, 451-458, 1981 discloses that a mayonnaise which is considered as a n acidic oil-in-water type emulsion, having good heat-stability, was prepared by using an egg yolk treated with phospholipase A (PL-A).

In this case, the enzyme used was obtained from porcine pancrease.

U.S. Pat. No. 4,034,124 discloses that oil-in-water emulsions having improved heat-stability can be prepared when a phospholipo-protein which has been modified by the action of PL-A is incorporated during some stage of the emulsion preparation. This patent also discloses that phospholipases other than PL-A do not bring about the desired characteristics of the patented product. A suitable source of PL-A for this patent is pancreatin which is preferably heat-treated, preferably under acidic conditions.

Thus, it has hitherto been difficult to obtain whole egg or egg yolk, which exhibits both excellent heat-gelation properties and emulsifying properties, by the use of PL-D of plant origin. Also whole egg or egg yolk prepared by the use of PL-A exhibits decreased heat-gelation properties.

The provision of egg yolks having improved properties, for example, heat-gelation ability such as gel strength and emulsifying properties, which are particularly advantageous for use in the preparation of certain foodstuffs, has continuously been desired.

BRIEF DESCRIPTION OF PREFERRED EMBODIMENTS

The present invention is based upon the discovery that properties of egg yolk or whole egg may unexpectedly be modified by treating with a PL-D of microorganism origin.

The present invention is directed to provide a process for modifying the properties of egg yolk for use in the preparation of foodstuffs.

According to one feature of the present invention, there is provided a process for modifying the properties of egg yolk, particularly for use in foodstuffs which comprises treating egg yolk with an effective amount of phospholipase D derived from a microorganism, thereby to convert phospholipids contained in said egg yolk into phosphatidic acid.

By this process of the present invention, it is possible to convert phospholipids such as, for example, phosphatidyl choline (PC) and phosphatidyl ethanolamine (PE), the most important functional factors present in egg yolk into phosphatidic acid (PA)

According to another feature of the present invention, we provide a process in which the egg yolk is treated with an effective amount of phospholipase A (PL-A) in combination with or after the treatment of the phospholipase D.

By the addition of PL-A, the resultant phosphatidic acid (PA) may further be converted into lyso-phosphatidic acid (LPA).

According to further aspect of the present invention, we provide a process wherein an effective amount of an edible compound having a hydroxy group is added to said egg yolk either prior to or simultaneously with the phospholipase D and/or phospholipase A treatment.

This further process allows the means whereby phospholipids may also be converted into base-exchanged phospholipids.

It has been observed that the phosphatidic acid (PA), lyso-phosphatidic acid (LPA) and base-exchanged phospholipids are capable of enhancing the desired properties of the egg yolk modified according to the present invention.

The egg yolk modified according to the present invention exhibits excellent properties, for example, higher heat-gelation and emulsification properties.

On the contrary, it may be difficult to obtain the desired results merely by the addition of PA and/or LPA to untreated egg yolk.

DETAILED DESCRIPTION OF PREFERRED EMBODIMENTS

The present invention is further described hereinbelow in the following specification.

The process steps according to the present invention may be exemplified as follows:

(1) In the case of using PL-D of microorganism origin; compounds of formula (i) represent phospholipids of egg yolk

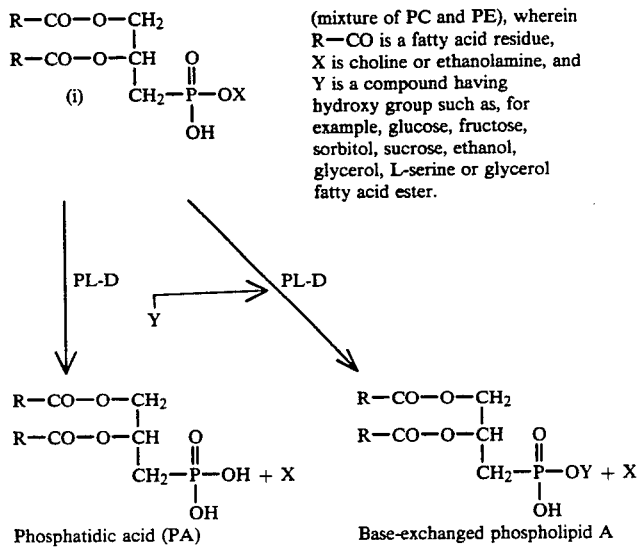

(2) In the case of using PL-D of microorganism origin and PL-A, the phospholipids of egg yolk are as described above for compounds of formula (i)

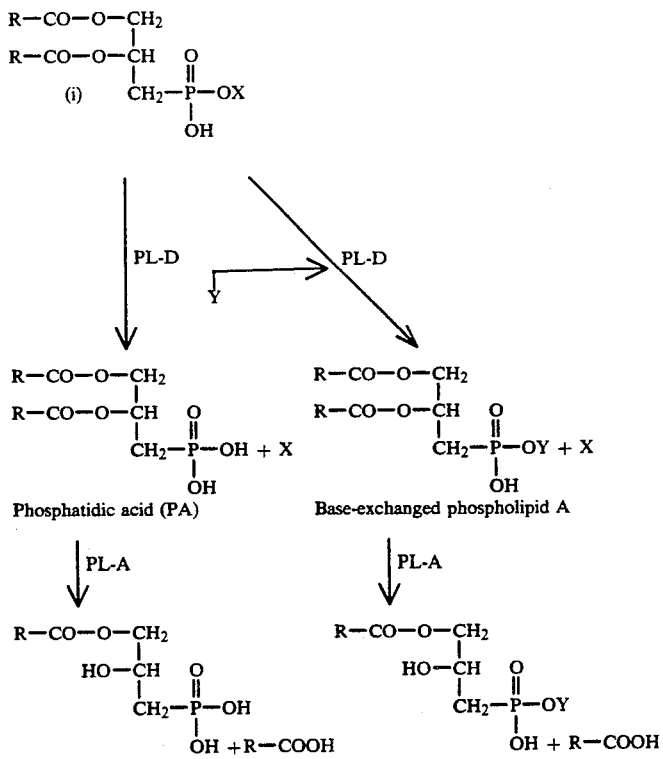

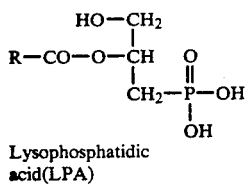
Lysophosphatidic acid(LPA)

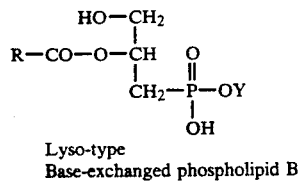
Lyso-type Base-exchanged phospholipid B

With reference to the above-mentioned processes, it is noted that the ester bond between the phosphoric acid portion and the base is hydrolyzed by the action of PL-D derived from a microorganism to liberate a base and phosphatidic acid (PA).

In the case where as edible compound having a hydroxy group (for example, glycerol) is used in combination with the enzyme, a transphosphatidylation reaction occurs so that base-exchanged phospholipids are formed by esterification coupling between the added hydroxy group and the phosphoric acid portion of the phospholipids.

In the case where PL-D derived from a microorganism is used in combination with PL-A, the ester bond between the hydroxy at the α- or β- position of, for example, glycerol and fatty acid is hydrolyzed to form lysophospholids.

For the purpose of the present invention, it is possible to use, for example, eggs of hens, ducks and quails, although it is possible, if desired, to use concentrated eggs, dried eggs and eggs treated with known enzymes such as, for example, protease and lipase. Untreated egg is preferably used. Untreated egg yolk or whole egg of hens are used throughout the Examples of this specification.

The egg yolk may preferably be used in the form of an aqueous solution and may contain egg white.

Examples of a microorganism from which the PL-D for use in the present invention may be obtained, include the enzymes originating from, for example, the genera Streptomyces, Bacillus, Aspergillus, Rhizopus, Mucor, Nocardiopsis, Brevibacterium, Micromonospora, Nocardia, Actinomdura and Saccharomyces.

Examples of PL-A which may be used for the purpose of the present invention include the enzymes of animal origin such as, for example, the enzymes originating from the pancreas of pigs and cattle as well as the enzyme derived from microorganisms.

The edible compound having a hydroxy group may be preferably added to egg yolk simultaneously with the addition of the PL-D.

Examples of edible compounds which may be used for the purpose of the present invention include glucose, fructose, sorbitol, sucrose, ethanol, glycerol, L-serine and glycerol fatty acid ester. These compounds may be used in the range of, for example, 1-20% (w/w) on the basis of the amount of egg yolk.

The egg yolk may e.g. be treated with the PL-D at a temperature of from 5° to 70° C. (preferably, 30°-60° C.) and at a pH of from 2 to 9 (preferably, 4-8) for a period of from 1 minute to 20 hours (preferably, from 6 to 5 hours). The amount of the PL-D for use may be, for example, from 0.5 to 1000 units (preferably 1-100 units) per 1 g of combined PC+PE contained in the egg used. In the case of PL-A, the enzyme may be used in a similar manner to the PL-D.

Preferred examples of edible compounds having a hydroxy group which may be used for the purpose of the present invention include glucose, fructose, sorbitol, sucrose, ethanol, glycerol, L-serine and glycerol fatty acid, from which base-exchanged phospholipids such as phosphatidyl glucose, phosphatidyl fructose, phosphatidyl sorbitol, phosphatidyl sucrose, phosphatidyl ethanol, phosphatidyl glycerol, phosphatidyl L-serine and phosphatidyl glycerol fatty acid ester may be produced.

Examples of lyso-type base-exchanged phospholipids include lyso-phosphatidyl glucose, lyso-phosphatidyl fructose, lyso-phosphatidyl sorbitol, lyso-phosphatidyl sucrose, lyso-phosphatidyl ethanol, lyso-phosphatidyl glycerol and lyso-phosphatidyl L-serine.

Egg yolk or whole egg modified by the process of the present invention may be used, for example, for the preparation of foodstuffs which particularly require improved heat-gelation properties such as higher gel strength and emulsifying properties, which include, for example, meat-processed foodstuffs, sponge cakes, tarts, biscuits, cookies, ice creams, doughnuts, mayonnaises, dressings, egg sheets, crepes and the like.

The following non-limiting examples and references illustrate the present invention.

EXAMPLE 1

On each occasion, a PL-D originating from a microorganism of the genus Streptomyces described in Reference 1 hereinafter (hereinafter referred to as PL-D R1) or a PL-D derived from carrot described in Reference 2 hereinafter (hereinafter referred to as PL-D R2) was added to an aqueous solution of egg yolk (500 ml; 70% w/v). The conversion ratio of phospholipids into PA by the action of enzyme PL-D (hereinafter referred to as conversion ratio) is shown in the following Table 2.

The solution was adjusted to a pH of 6.0 and a temperature of 50° C. for 4 hours to obtain the results shown in Table 2.

The activity of the enzyme was measured as follows:
0.5 ml of 6% (w/v) aqueous solution of purified soyabean lecithin was mixed with 0.5 ml of 50 mM tris—HCl buffered solution (pH 7.0). To the mixture was added an enzyme solution (0.01 ml) to carry out the reaction at a temperature of 37° C. for 10 minutes. Then, the reaction was discontinued by adding an aqueous solution of 15% trichloroacetic acid (0.5 ml). Determiner ChE (commercial product of Kyowa Medex K.K., Japan) was used to measure the amount of the resultant choline in the solution.

Separately, a similar measurement was effected for control purpose by using the enzyme which had previously been inactivated by heating. An enzymatic activity capable of liberating 1 μmol/min. of choline was designated as 1 unit.

In order to determine the conversion ratio as defined above, choline was quantitatively measured using Determiner ChE (reagent for measuring choline-esterase; commercial product of Kyowa Medex K.K., Japan). The conversion ratio of phosphatidyl choline (PC) into phosphatidic acid (PA) by the action of the enzyme in egg yolk as calculated on the basis of the amount of the resultant choline. The conversion ratio of phosphatidyl ethanolamine (PE) present in the egg yolk by the action of the enzyme was deemed as the same as the conversion ratio of PC present in the egg yolk. The phospholipid composition was extracted from the solution by using a solvent (chloroform/methanol, 2:1 v/v) under acidic conditions and its presence was determined by thin layer chromatography using a silica gel plate 60, Art. 5721, commercial product of Merck AG., West Germany.

The conversion ratio (mol %) of phospholipids into PA by the action of PL-D was expressed by (PA)/(PC+PE)×100.

TABLE 2

| Enzyme used | U | A |
|---|---|---|
| PL-D R1 | 6.25 | 51 |
| PL-D R2 | 6.25 | 0 |

Notes:
U-Amount of PL-D added, expressed by the activity unit per 1 g of PC + PE;
A-Conversion ratio (mol %) into PA by the action of the enzyme.

This table indicates that PL-D R1 is capable of converting phospholipids contained in lipoprotein of egg yolk, in comparison with PL-D R2.

EXAMPLE 2

A similar procedure to that described in Example 1 was carried out by the use of 500 g of whole egg instead of an aqueous solution of egg yolk (70% w/v) to obtain the results shown in the following Table 3.

TABLE 3

| Enzyme used | U | A |
|---|---|---|
| PL-D R1 | 6.25 | 59 |
| PL-D R2 | 20.0 | 0 |

Notes:
See Table 2.

This table indicates that a similar result to the result described above is obtained by using a whole egg.

EXAMPLE 3

Either PL-D R1 (6.25 units) or PL-D R2 (20 units) was added to an aqueous solution of egg yolk (70% w/w). The solution was adjusted to a pH of 6.0 and heated at a temperature of 50° C. for 4 hours to obtain an aqueous solution of egg yolk treated with the enzyme. Separately, to an aqueous solution of egg yolk (500 ml; 70% w/v) was added soyabean phosphatidic acid in an amount of 50 mol % on the basis of the total amount of PC and PE originally in the egg yolk. The mixture was treated in a similar manner to that described above, without using the enzyme, to obtain a sample (Sample D).

The results are shown in the following Table 4.

TABLE 4

| Enzyme used | U | A |
|---|---|---|
| PL-D R1 | 6.25 | 54 |
| PL-D R2 | 20.0 | 0 |
| D | — | 0 |

Notes:
See Table 2.

Then, on each occasion, the sample was put into a casing having a diameter of 3 cam and heated at a temperature of 90° C. for 40 minutes to obtain a heat-coagulated gel having a diameter of 3 cm and a heat of 3 cm. The stress required for the deformation of 5 mm of the gel was measured to express the hardness of the gel. A creepmeter (Yamaden RE-3305: commercial product of Yamaden K.K., Japan) was used to measure the amount of load and the degree of deformation by insertion of a plunger having a diameter of 7 mm into the gel.

The results are shown in Table 5.

TABLE 5

| Enzyme used | H | L | DE |
|---|---|---|---|
| PL-D R1 | 10.7 | 355 | 6.4 |
| PL-D R2 | 3.5 | 111 | 5.8 |
| D | 4.8 | 97 | 5.5 |

Notes:
H-Hardness ($\times 10^4$ dyne/cm$^2$);
L-Breaking load (g);
DE-Breaking deformation (mm)

It was observe that the gel strength of PL-D R1-treated product according to the present invention is far superior in comparison with other samples. It was also noted that egg yolk having better gel-forming ability may be obtained by the process of the present invention.

It has been found that the improved results obtained by the process of the present invention can not be obtained merely by adding to egg yolk a corresponding phospholipid (phosphatidic acid) in the absence of any enzymatic treatment according to the present invention.

EXAMPLE 4

On each occasion, to an aqueous solution of egg yolk (500 ml; 70% w/v), PL-D R1 having the activity unit (U) shown in the following Table 6 was added. The solution was adjusted to a pH of 6.0 and was treated at a temperature of 50° C. for 1-2 hours to obtain an aqueous solution of yolk having the conversion ratio shown in Table 6. Then the solution was treated in a same manner to that described in Example 3 to obtain gels having the physical properties as shown in Table 6,

TABLE 6

| A | H | L | DE | U | T |
|---|---|---|---|---|---|
| 0 | 0.93 | 128 | 8.0 | 0 | 1 |
| 12 | 1.28 | 156 | 7.7 | 2 | 1 |
| 32 | 1.57 | 212 | 9.6 | 5 | 1 |
| 34 | 1.98 | 307 | 10.2 | 10 | 1 |
| 41 | 2.51 | 394 | 10.3 | 20 | 1 |
| 53 | 2.75 | 510 | 10.3 | 20 | 3 |

Notes:
A-Conversion ratio (mol %);
H, L and DE-See Table 5;
U-See Table 2;
T-Reaction time (hour)

This table suggests the gel-forming ability of egg yolk may be improved by increasing the conversion ratio of phospholipid of egg yolk (mol %).

EXAMPLE 5

On each occasion, to an aqueous solution of egg yolk (500 ml; 70 % w/v), PL-D R1 (6.25 units) or a mixture of the PL-D R1 with glycerol (10% v/v) was added. The solution was adjusted to a pH of 6.0 and treated at a temperature 50° C. for 4 hours to obtain an aqueous solution of yolk treated with the enzyme. The solution was then treated in a similar manner to that described in Example 3 to obtain a gel having the properties as shown in Table 7.

TABLE 7

| Additive | H | L | DE |
|---|---|---|---|
| PL-D R1 | 9.9 | 400 | 9.0 |

TABLE 7-continued

| Additive | H | L | DE |
|---|---|---|---|
| Control 1 | 4.1 | 110 | 6.0 |
| PL-D R1 plus glycerol | 6.6 | 394 | 12.0 |
| Control 2 | 4.1 | 100 | 5.0 |

Notes;
H, L and DE-See Table 5;
Control 1-containing no PL-D;
Control 2-containing glycerol and no PL-D.

It was observed that a highly extendable gel having a higher breaking deformation was obtained by a combined use of glycerol and PL-D for treating an aqueous solution of egg yolk, in comparison with the use only of PL-D, presumably because phospholipid of lipoprotein may be converted into phosphatidyl glycerol which also serves to enhance, for example, the strength and heat gelatin properties.

EXAMPLE 6

On each occasion, one member selected from PL-D R1 (7 units), PL-D R2 (20 units) and Lectitase (20 units: this is a PL-A originating from the pancrease of pig; commercial product of Novo Industry, Sweden) was added to an aqueous solution of egg yolk (500 ml; 70% w/v). The mixture was adjusted to a pH of 6.0 and treated at a temperature of 50° C. for 4 hours to obtain an aqueous solution of enzyme-treated yolk. The results are shown in the following Table 8.

The term "No enzyme" used hereinafter denotes a sample containing no enzyme.

TABLE 8

| Enzyme | A | B |
|---|---|---|
| PL-D R1 | 48 | 0 |
| PL-D R2 | 0 | 0 |
| PL-A | 0 | 91 |
| No enzyme | 0 | 0 |

Notes:
A-Conversion ratio (mol %) by the action of PL-D;
B-Conversion ratio (mol %) by the action of PL-A.

Determiner NEFA (reagent for quantitative determination of free fatty acid; commercial product of Kyowa Medex K.K., Japan) was hereinafter used to determine the conversion ratio obtained by PL-A added to egg yolk on the basis of the ratio of the total amount of PC and PE to the amount of fatty acid which was newly formed by the reaction.

Then, on each occasion, a mayonnaise was prepared using the above-mentioned yolk solution treated with the enzymes, the ratios of the materials used being shown in the following Table 9.

TABLE 9

| Material | Amount (% w/w) |
|---|---|
| Frying oil* | 74.0 |
| Table salt | 1.5 |
| Mustard powder | 1.5 |
| Acetic acid** | 4.5 |
| Water | 11.5 |
| Yolk*** | 7.5 |

Notes:
*soyabean oil (named as Shirashimeyu in Japan);
**10% v/v aqueous solution;
***Aqueous solution.

The resultant mayonnaise was kept at a temperature of 37° C. for one hour. Then a creepmeter was used to measure the stress by inserting a plunger having a diameter of 4 cm into the product at a depth of 5 mm.

The viscosity of the mayonnaise was indicated on the basis of the hardness obtained by the measurement and is shown in the following Table 10.

TABLE 10

| Additive | H | V |
|---|---|---|
| PL-D R1 | 6.5 | 2.7 |
| PL-D R2 | 2.2 | 0.9 |
| PL-A | 4.4 | 1.8 |
| No enzyme | 2.4 | 1.0 |

Notes:
H-See Table 6;
V-Relative value calculated on the basis of "No enzyme".

These results suggest that, although the hardness of the emulsified product may be increased by the use of PL-A, it is possible to increase the hardness further by treatment with PL-D R1 above, according to the present invention.

EXAMPLE 7

On each occasion, to 70% (w/v) aqueous solution (500 ml) was added PL-D R1 to carry out the reaction for 4 hours, followed by addition of PL-A to carry out the reaction for 4 hours. Then, glycerol was added to each sample in an amount of 5.15% (w/w) for treating under the following conditions.

TABLE 11

| Sample | Enzyme | PH | Temp. | Time | Glycerol |
|---|---|---|---|---|---|
| 1 | PL-D R1 (6.25 U) | 6.0 | 50° C. | 8 hr. | 5% |
|   | PL-A (20 U) | 6.0 | 50° C. | 4 hr. |   |
| 2 | PL-D R1 (6.25 U) | 6.0 | 50° C. | 8 hr. | 15% |
|   | PL-A (20 U) | 6.0 | 50° C. | 4 hr. |   |
| 3 | No enzyme | 6.0 | 50° C. | 8 hr. | 0 |

Each sample was used to prepare a mayonnaise in a similar manner to that described in Table 9. The properties of the products were measured in a similar manner to that described in Example 6.

The results are shown in the following Table 12.

TABLE 12

| Sample | H | V |
|---|---|---|
| 1 | 12.5 | 4.0 |
| 2 | 15.8 | 5.1 |
| 3 | 3.1 | 1.0 |

Notes:
See Table 10.

This table indicates that the hardness of the resultant mayonnaise was increased by the use of enzyme-treated egg yolk comprising lyso-type base-exchanged translocation product.

EXAMPLE 8

PL-D R1 (6.25 units) was added to 500 ml of an aqueous solution of egg yolk (70% w/v). The mixture was treated in a similar manner to that described in Example 1 to obtain an aqueous solution of enzyme-treated yolk having a conversion ratio of 47.9 mol % by the action of PL-D R1.

By using the egg yolk solution, meat gels were prepared as follows.

On each occasion, 30 g of an aqueous solution of enzyme-treated egg yolk, an aqueous solution of untreated egg yolk or water was mixed with a minced ham (150 g). After removal of air, each sample was put into a casing and heated at a temperature of 70° C. for 20 minutes to obtain a meat gel. The amount of water (% w/w, calculated on the basis of the weight of water before heating) liberated from the meat gel was measured and shown in Table 11.

TABLE 13

| Sample | A (mol %) | Water (% w/w) |
|---|---|---|
| 1 | 47.9 | 5.1 |
| 2 | 0 | 9.8 |
| 3 | — | 15.3 |

Notes:
1-Enzyme-treated egg yolk;
2-Untreated egg yolk;
3-Water alone:
A-Conversion ratio by PL-D.

It was observed that the water-holding ability of the meat product was significantly improved by the use of an aqueous solution of enzyme-treated yolk according to the present invention.

EXAMPLE 9

An aqueous solution of egg yolk (500 ml; 70% w/v) and PL-D R1 (4 units) was treated in the same manner as that described in Example 1 to obtain an aqueous solution of enzyme-treated egg yolk having a conversion ratio of 28 mol %. This solution was used to prepare meat gels in the following manner.

On each occasion, sodium chloride (6 g), Polygon C (1 g; polymerized phosphate, commercial product of Chiyoda Kagaku Kogyosho, Japan), an aqueous solution of sodium nitrite (30 g; 5%; 1 ml) and an aqueous solution (30 g) of egg yolk (enzyme-treated or untreated) was added to minced ham (200 g). After removal of air, the mixture was put into a casing and heated at a temperature of 70° C. for 20 minutes to obtain a meat gel.

The properties of the resultant gels are shown in the following Table 12.

TABLE 14

| Sample | A (mol %) | L (g) | DE (mm) |
|---|---|---|---|
| 1 | 2.9 | 991 | 13.1 |
| 2 | 0 | 764 | 11.4 |

Notes:
1-Enzyme-treated;
2-Untreated;
A-Conversion ratio by PL-D R1;
L-Breaking load;
DE-Breaking deformation.

This table indicates that, by using an aqueous solution of enzyme-treated egg yolk, the gel-strength of the product was significantly increased.

EXAMPLE 10

On each occasion, an aqueous solution of egg yolk (500 ml; 70% w/w) was used to obtain the following samples:
Sample 1 containing PL-D R1;
Sample 2 prepared by adding PL-D R1, followed by adding Lecitase (PL-A) 4 hours later;
Sample 3 containing PL-D R2;
Sample 4 containing Lecitase (PL-A);
Sample 5 without addition of enzyme.

The reaction conditions and the results are shown in the following Table 15.

TABLE 15

| Sample | A | B | Treating conditions |
|---|---|---|---|
| 1 | 48 | 0 | PL-D R1 (6.25 units); pH 6.0; 50° C., 4 hr |
| 2 | 54 | 93 | PL-D R1 (6.25 units); PL-A (20 units): PL-D R1 (pH 6.0; 50° C.; 8 hr); PL-A (pH 6.0; 50° C.; 4 hr). |
| 3 | 0 | 0 | PL-D R2 (20 units), pH 6.0; 50° C.; 4 hr. |
| 4 | 0 | 91 | PL-A (20 units), pH 6.0; 50° C.; 4 hr |
| 5 | 0 | 0 | No enzyme; pH 6.0; 50° C.; 4 hr |

Notes:
A-Conversion ratio by PL-D (mol %);
B-Conversion ratio by PL-A (mol %).

On each occasion, mayonnaise was prepared by using the above-mentioned sample of the aqueous solution and the materials shown in Table 9. The results are shown in Table 16.

TABLE 16

| Used sample | H | RV |
|---|---|---|
| 1 | 6.5 | 2.7 |
| 2 | 17.1 | 7.1 |
| 3 | 2.3 | 1.0 |
| 4 | 4.4 | 1.8 |
| 5 | 2.4 | 1.0 |

Notes:
H-Hardness ($\times 10^4$ dyne/cm$^2$);
RV-Relative value on the basis of the hardness obtained by using Sample No. 5 (No enzyme).

It was observed that the hardness of No. 1 was higher than the corresponding values of Nos. 3 and 4, whilst the hardness of No. 2 was the highest.

EXAMPLE 11

Aqueous solutions of enzyme-treated yolk shown in the following Table 15 were prepared in a similar manner to that described in Example 9 except the samples containing the following enzymes:
Sample 1 (PL-D R1 5 units),
Sample 2 (PL-D R1 5 units and PL-A 10 units),
Sample 3 (PL-D R2 20 units) and
Sample 4 (PL-A 10 units).

On each occasion, the solution was treated in a similar manner to that described in Example 3 to obtain a gel. The results are shown in the following tables.

TABLE 17

| Sample | A | B |
|---|---|---|
| 1 | 34 | 0 |
| 2 | 46 | 64 |
| 3 | 0 | 0 |
| 4 | 0 | 72 |
| 5 | 0 | 0 |

Notes:
A-Conversion ratio by PL-D (mol %);
B-Conversion ratio by PL-A (mol %)

TABLE 18

| Sample | H | L | DE |
|---|---|---|---|
| 1 | 6.8 | 273 | 12.9 |
| 2 | 11.4 | 482 | 14.0 |
| 3 | 4.2 | 143 | 9.2 |
| 4 | 1.5 | 29 | 6.6 |
| 5 | 4.8 | 191 | 9.6 |

Notes:
H-Hardness ($\times 10^4$ dyne/cm$^2$);
L-Breaking load (g);
DE-Breaking deformation (mm).

It was observed that Sample 1 is better than Samples 3 and 4, while Sample 2 is the best with respect to hardness, breaking load and breaking deformation.

EXAMPLE 12

On each occasion, to an aqueous solution of egg yolk (500 ml; 70% w/w) was added PL-D R1, PL-A or a mixture of PL-D R1 and PL-A in the activity unit shown in the following Table 17. The mixed solution was adjusted to a pH of 6.0 and treated at a temperature of 50° C. for 4 or 8 hours to obtain an aqueous solution of enzyme-treated yolk, of which conversion ratio is shown in Table 19. The resultant aqueous solution of yolk was treated in a similar manner to that described in Example 3 to obtain a gel, of which physical characteristics are shown in Table 19.

TABLE 19

| A  | B  | H    | L   | DE  | UA  | TA | UB | TB |
|----|----|------|-----|-----|-----|----|----|----|
| 0  | 0  | 4.3  | 153 | 6.4 | 0   | 4  | 0  | 4  |
| 34 | 0  | 6.8  | 175 | 5.2 | 5   | 4  | 0  | 4  |
| 0  | 72 | 1.5  | 25  | 3.5 | 0   | 4  | 10 | 4  |
| 21 | 40 | 6.0  | 131 | 4.7 | 2.5 | 4  | 5  | 4  |
| 34 | 82 | 2.9  | 64  | 5.1 | 5   | 4  | 10 | 8  |
| 43 | 77 | 5.4  | 136 | 5.5 | 5   | 4  | 10 | 4  |
| 50 | 64 | 11.4 | 306 | 5.8 | 4   | 8  | 8  | 4  |
| 55 | 40 | 12.6 | 320 | 5.8 | 7.5 | 4  | 5  | 4  |
| 56 | 76 | 10.0 | 340 | 7.7 | 7.5 | 4  | 10 | 4  |

Notes:
A-Conversion ratio by PL-D R1 (mol %);
B-Conversion ratio by PL-A (mol %);
H-Hardness ($\times 10^4$ dyne/cm$^2$);
L-Breaking load (g);
DE-Breaking deformation (mm);
UA-Amount of PL-D R1 added (unit);
TA-Reaction time (hour) of PL-D R1;
UB-Amount of PL-A added (unit);
TB-Reaction time (hour) of PL-A.

This table indicates that modified egg yolks having different properties may be obtained by changing the conversion ratios (mol %) of PL-D R1 and PL-A.

EXAMPLE 13

PL-D R1 (2 units) was added to a solution of whole egg. The mixed solution was adjusted to a pH of 6.0 and treated at a temperature of 50° C. for 4 hours. PL-A (5 units) was added thereto. The solution was then treated at a temperature of 50° C. for 4 hours to obtain an aqueous solution of whole egg treated with the enzymes. The solution was used to obtain a sample gel in a similar manner to that described in Example 3. Separately a control gel was prepared in a similar manner to that described in Example 3.

The physical properties of the gels are shown in the following Table 20.

TABLE 20

|         | A  | B  | H   | L   | DE  |
|---------|----|----|-----|-----|-----|
| Control | 0  | 0  | 7.3 | 238 | 6.4 |
| Sample  | 22 | 40 | 9.7 | 382 | 7.7 |

Notes:
A-Conversion ratio by PL-D (mol %);
B-Conversion ratio by PL-A (mol %);
H-Hardness ($\times 10^4$ dyne/cm$^2$);
L-Breaking load (g);
DE-Breaking deformation (mm).

These results indicate that gel strength of whole egg can significantly be improved according to the present invention.

EXAMPLE 14

To an aqueous solution of yolk (500 ml; 70% w/v) was added PL-D R1 (7units). After adjusting to a pH of 6.0, the mixed solution was treated at a temperature of 50° C. for 4 hours. To the treated solution was added PL-A (20 units). The mixture was treated in a similar manner to that described above to obtain an aqueous solution of yolk treated with the enzymes. The product was designed as Sample No. 1.

Separately, soyabean phosphatidyl choline (10 g) was dispersed in water (500 ml). PL-D R1 (500 unit) was added to the material to carry out the reaction at a temperature of 50° C. for 12 hours. The PL-A (Lectanase; 1000 unit) was added to the resultant solution to carry out a further reaction at a temperature of 65° C. for 12 hours. After completion of the second reaction, the resultant solution was freeze-dried. The dried material was dissolved in n-hexane (100 ml). The solution was centrifuged to remove precipitates. After removal of n-hexane, the material was dispersed in water (200 ml) and freeze-dried to obtain a sample of lysophosphatidic acid (LPA)

To a similar aqueous solution of yolk was added the resultant LPA in an amount of 50 mol % calculated on the basis of the total amount of PC and PE to obtain a product designed as Sample No. 2.

On each occasion, Sample 1 to 2 was used to prepare a gel in a similar manner to that described in Example 3. The physical properties of the resultant gels are shown in the following Table 21. In this table, Sample No. 3 denotes a gel produced without the use of enzyme.

TABLE 21

| Sample | A  | B  | H    | L   | DE   |
|--------|----|----|------|-----|------|
| 1      | 56 | 90 | 11.4 | 482 | 14.0 |
| 2      | 0  | 0  | 2.4  | 62  | 5.3  |
| 3      | 0  | 0  | 4.8  | 191 | 9.6  |

Notes:
A-Conversion ratio by PL-D (mol %);
B-Conversion ratio by PL-A (mol %);
H, L and DE-See Table 20.

These results indicate that heat-gel forming properties of egg yolk may significantly be improved by treating lipoprotein with PL-D and PL-A according to the present invention. It was difficult to obtain egg yolk having increased gel-forming ability merely by adding the corresponding LPA to untreated egg yolk.

EXAMPLE 15

An aqueous solution of egg yolk (500 ml; 70% w/v), PL-D R1 (7 units) and PL-A (2 units) was treated in a similar manner to that described in Example 13 to obtain an aqueous solution of egg yolk treated with the enzymes. The resultant solution was then used to prepare a meat gel in the following manner.

Sodium chloride (0.5 g) and the aqueous solution of enzyme-treated yolk (20 g) were added to a mined ham (100 g) and mixed for 5 seconds by using a food cutter for home use, followed by further mixing using a mixer under reduced pressure. The resultant mixture was put into a casing and heated at a temperature of 70° C. for 20 minutes to obtain a meat gel.

Separately, a control meat gel was produced in a similar manner to that described above using an aqueous solution of yolk without using the enzymes.

A creepmeter and a plunger having a diameter of 5 mm were used to measure the breaking load and breaking deformation. The results are shown in Table 22.

TABLE 22

|        | A  | B  | L   | DE  |
|--------|----|----|-----|-----|
| Sample | 60 | 23 | 450 | 3.8 |

TABLE 22-continued

|  | A | B | L | DE |
|---|---|---|---|---|
| Control | 0 | 0 | 355 | 3.1 |

Notes:
A-Conversion ratio by PL-D (mol %);
B-Conversion ratio by PL-A (mol %):
L and DE-See Table 20.

Further, a meat gel was prepared in the following manner:

To a minced ham (100 g) was added sodium chloride (3 g), Polygon (0.5 g), 5% sodium nitrite (0.5 ml) and the aqueous solution of yolk treated with the enzymes (30 g). After mixing for 30 seconds using a food cutter for home use, followed by removal of air for 30 seconds using a mixer under reduced pressure, the resultant mixture was put into the casing and heated at a temperature of 70° C. for 20 minutes to obtain a meat gel used for control purpose.

The physical properties of the sample gel and control gel are shown in Table 23.

TABLE 23

|  | A | B | L | DE |
|---|---|---|---|---|
| Sample | 60 | 23 | 725 | 7.4 |
| Control | 0 | 0 | 663 | 6.3 |

Notes:
A-Conversion ratio by PL-D (mol %);
B-Conversion ratio by PL-A (mol %);
L and DE-See Table 20.

It was observed that the sample exhibited better breaking load and breaking deformation than that of the control gel.

REFERENCE 1

A medium (15 l; pH 7.0) containing glycerol (2%), peptone (2%), potassium nitrate (0.2%), potassium dihydrogen phosphate (0.05%), magnesium sulfate (0.05%), sodium chloride (0.05%) was put into a jar fermentor having a capacity of 30l. The medium was sterilized at a temperature of 120° C. for 20 hours.

Separately, *Streptomyces lavendulae* IFO 3125 was cultured at a temperature of 28° C. for 20 hours using a medium having the same composition as above to obtain a seed.

The seed (500 ml) was transferred to a similar main medium for culturing at a temperature of 28° C. for 20 hours with aeration (15 l/min.) and stirring (250 r.p.m.). About 20 hours after the beginning of culturing, a highest enzymatic activity (1.2 U/ml) of the cultured broth was noted.

After removal of the cells from the cultured broth (15 l) by centrifugation (10,000 r.p.m./10 min), the supernatant (15 l) was concentrated under reduced pressure to 3 l, to which was then added ethanol (3 l) to remove precipitate. After further addition of ethanol (7 l), the concentrated solution was allowed to stand for removal of the supernatant. The resultant precipitate was dissolved in 50 mM tris—HCl buffered solution (1 l; pH 7.5). The solution was dialyzed against a buffered solution (15 l) having the same composition to remove low molecular weight impurities. The dialyzed solution was concentrated and purified by chromatography using a gel filtrating agent (Sephadex G-100, commercial product of Pharmacia Fine Chemicals AB, Sweden) to obtain an enzyme preparate which yielded an activity of 75%.

REFERENCE 2

Carrot (1 kg) was washed with water, treated with a mixer and homogenized (10,000 r.p.m./5 min.) while cooling with ice. The resultant solution was filtered using a gauze to give a filtrate. The filtrate was centrifuged (10,000 r.p.m./30 min.) to obtain a crude solution of carrot P-LD (10 units/ml) in the form of a supernatant.

We claim:

1. A process for improving the heat gelation properties of egg yolk, which process comprises treating egg yolk with an effective amount of a phospholipase D derived from a culture of a phospholipase D-generating microorganism selected from the group consisting of the genera Streptomyces, Bacillus, Nocardiopsis, Micromonospora, Nocardia, Brevibacterium, Actinomdura and Saccharomyces, to convert phospholipids contained in said egg yolk into phosphatidic acid.

2. The process according to claim 1, in which said egg yolk further comprises egg white.

3. The process according to claim 1, in which said egg yolk is in an aqueous solution.

4. The process according to claim 1, in which the amount of phospholipase D is from 0.5 to 1000 units per 1 g of the total of phosphatidyl choline and phosphatidyl ethanolamine contained in said egg yolk.

5. The process according to claim 1, in which said microorganism is *Streptomyces lavendulae* (IFO 3125).

6. The process according to claim 1, in which said egg yolk is further treated by contacting said egg yolk with an effective amount of a phospholipase A in combination with or after the treatment with the phospholipase D to convert said phosphatidic acid into lyso-phosphatidic acid.

7. The process according to claim 6, in which the effective amount of said phospholipase A is from 0.5 to 1000 units per 1 g of the total of phosphatidyl choline and phosphatidyl ethanolamine contained in said egg yolk.

8. The process according to claim 1 or 6 wherein an effective amount of an edible compound having a hydroxy group is added to said egg yolk either prior to or simultaneously with the phospholipase D and/or phospholipase A treatment.

9. The process according to claim 8, in which the compound having a hydroxy group is selected from glucose, fructose, sorbitol, sucrose, ethanol, glycerol, L-serine and glycerol fatty acid ester.

10. The process according to claim 1 or 6, in which said egg yolk is heated to a temperature of from 5° to 70° C. and at a pH of from 2 to 9 for a period of from 1 minute to 20 hours.

11. A foodstuff comprising the improved egg yolk prepared according to the process of claim 1 or 6.

12. In a process for the preparation of a foodstuff having an emulsifier and comprising a heat processing step, the improvement comprising the use of the egg yolk prepared according to claim 1 or claim 6 as said emulsifier.

13. In a process for the preparation of a foodstuff, said process comprising a heat gelation step, the improvement comprising the use of the egg yolk prepared according to claim 1 or claim 6 as a heat gelation agent.

14. In a process for the preparation of emulsions comprising water and oil phases, the improvement comprising the step of using the improved egg yolk prepared according to claim 1 or claim 6 as an emulsifying agent.

* * * * *